(12) United States Patent
Endo

(10) Patent No.: US 9,554,921 B2
(45) Date of Patent: Jan. 31, 2017

(54) MOVEMENT SUPPORT APPARATUS

(71) Applicant: Sony Corporation, Tokyo (JP)

(72) Inventor: Ken Endo, Tokyo (JP)

(73) Assignee: Sony Corporation, Tokyo (JP)

(*) Notice: Subject to any disclaimer, the term of this patent is extended or adjusted under 35 U.S.C. 154(b) by 94 days.

(21) Appl. No.: 14/320,732

(22) Filed: Jul. 1, 2014

(65) Prior Publication Data

US 2015/0018975 A1 Jan. 15, 2015

(30) Foreign Application Priority Data

Jul. 10, 2013 (JP) ................................. 2013-144490

(51) Int. Cl.
*A61F 2/66* (2006.01)
*A61F 2/70* (2006.01)
*A61F 2/50* (2006.01)
*A61F 2/68* (2006.01)

(52) U.S. Cl.
CPC .............. *A61F 2/6607* (2013.01); *A61F 2/66* (2013.01); *A61F 2002/5039* (2013.01); *A61F 2002/5073* (2013.01); *A61F 2002/6657* (2013.01); *A61F 2002/6836* (2013.01); *A61F 2002/701* (2013.01)

(58) Field of Classification Search
CPC ................. A61F 2002/5039; A61F 2002/5073
See application file for complete search history.

(56) References Cited

U.S. PATENT DOCUMENTS

| 2004/0243253 | A1* | 12/2004 | Cool .................... A61F 2/60 623/52 |
| 2010/0113980 | A1* | 5/2010 | Herr et al. ..................... 600/587 |
| 2014/0330393 | A1* | 11/2014 | Ward et al. ..................... 623/24 |

FOREIGN PATENT DOCUMENTS

JP 2012-501739 A 1/2012

OTHER PUBLICATIONS

U.S. Appl. No. 61/819,049, filed May 3, 2013.*

* cited by examiner

*Primary Examiner* — David H Willse
(74) *Attorney, Agent, or Firm* — Wolf, Greenfield & Sacks, P.C.

(57) ABSTRACT

There is provided a movement support apparatus including a lower limb coupling portion configured to be coupled to a lower limb, an elastic member, a ground contact unit configured to include a ground contact plate coming into contact with a surface and a transmission portion transmitting force generated by the elastic member, and an ankle portion configured to be installed between the lower limb coupling portion and the ground contact unit. The ground contact unit is installed to be displaceable between a position at which the transmission portion comes into contact with the ankle portion and a position at which the transmission portion is uncoupled from the ankle portion.

11 Claims, 15 Drawing Sheets

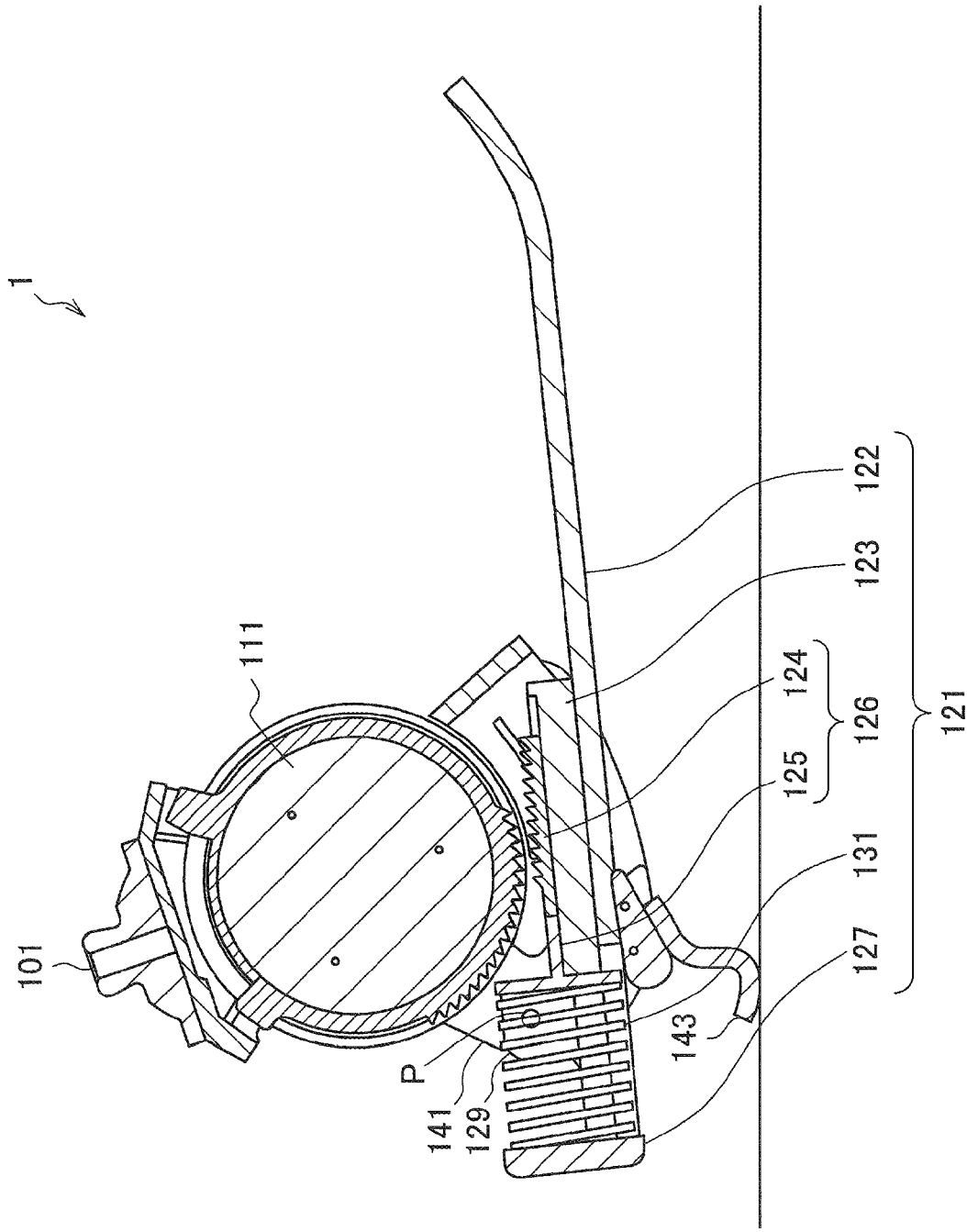

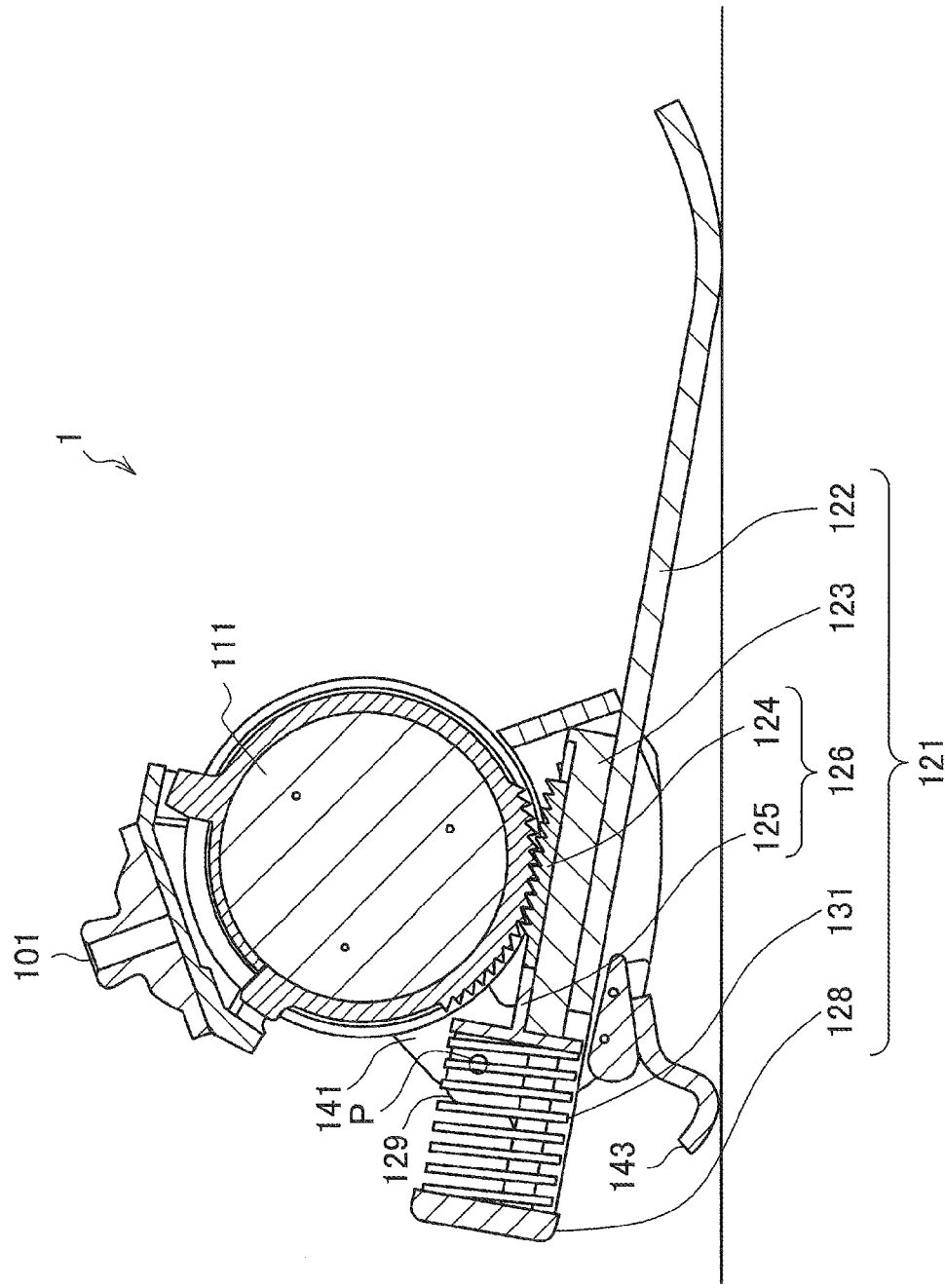

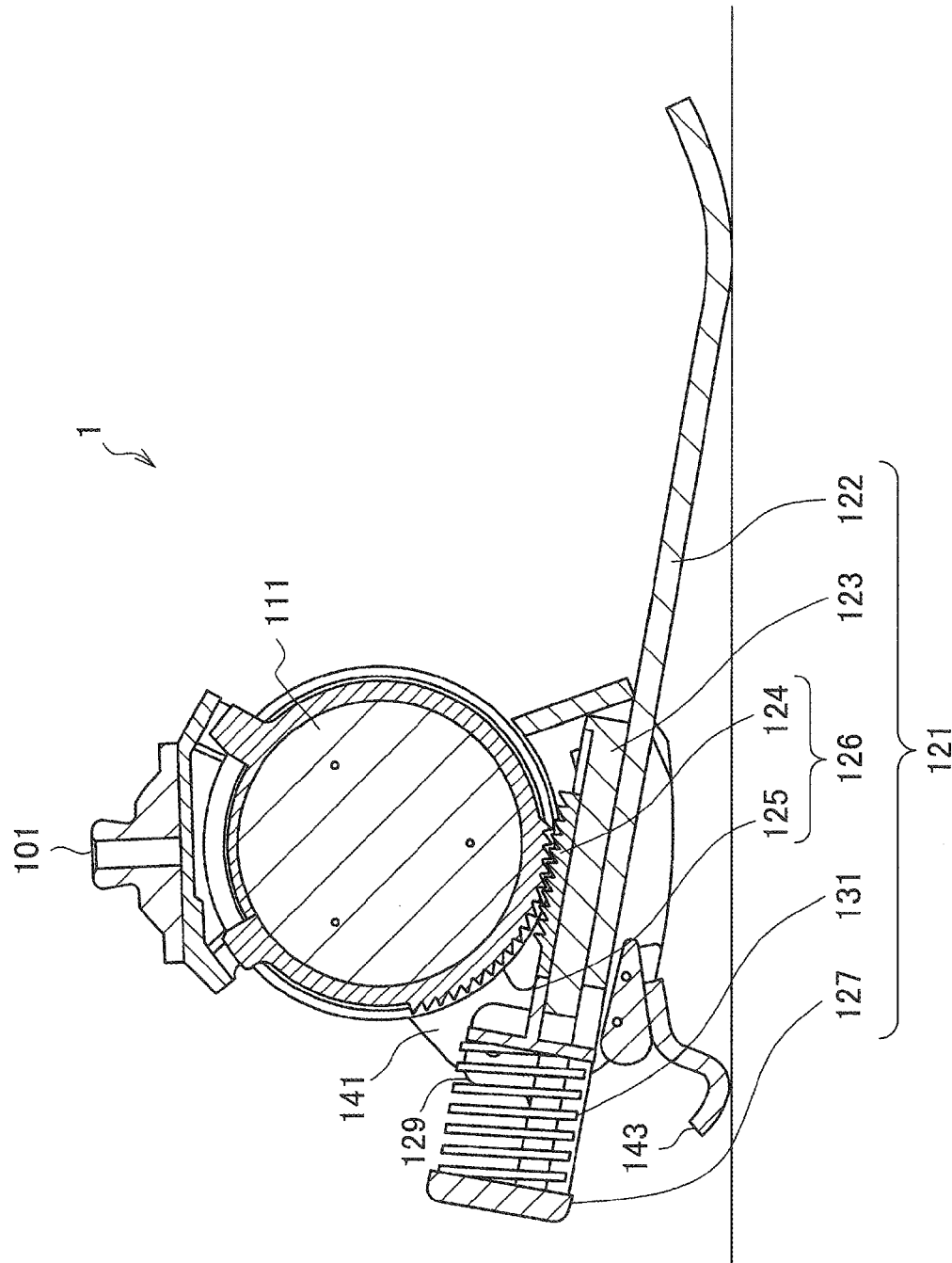

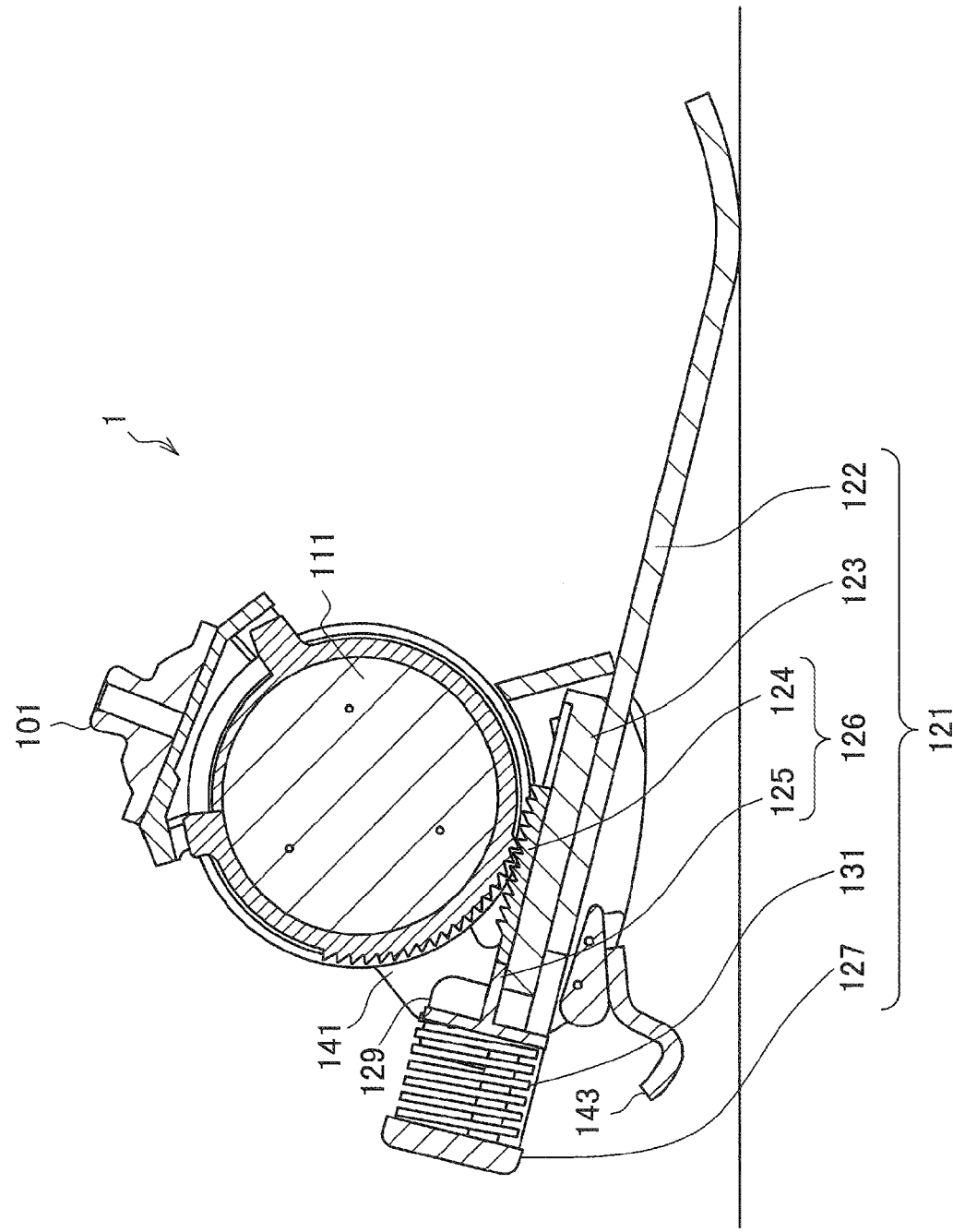

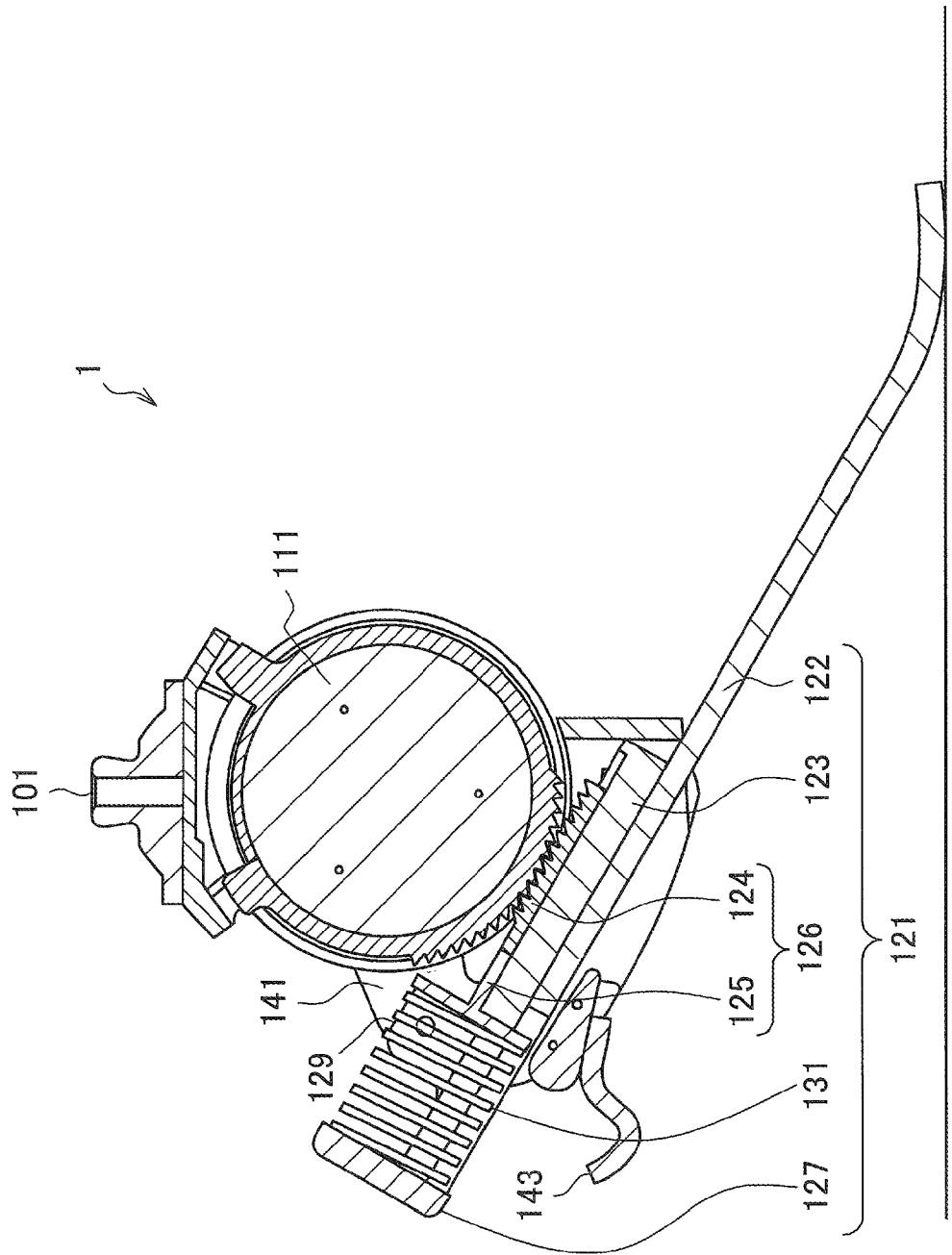

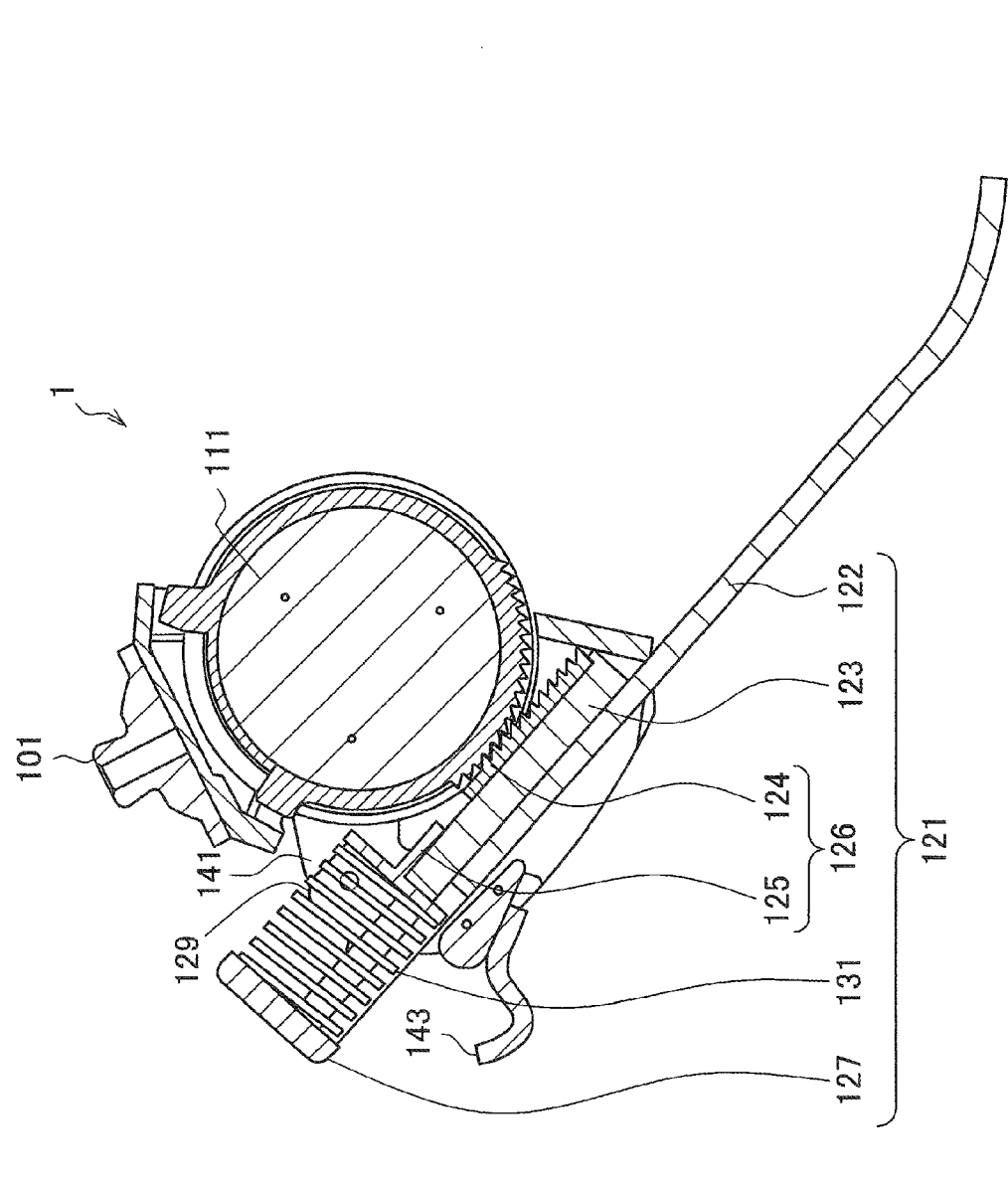

MOVEMENT SUPPORT APPARATUS

CROSS REFERENCE TO RELATED APPLICATIONS

This application claims the benefit of Japanese Priority Patent Application JP 2013-144490 filed Jul. 10, 2013, the entire contents of which are incorporated herein by reference.

BACKGROUND

The present disclosure relates to a movement support apparatus.

In recent years, biomechanics, in which structures and movement functions of living things are mechanically analyzed, has been actively studied. Further, development of products reducing burdens on human bodies or products to which the structures and movements of living things using such biomechanics are applied has been advanced.

In particular, many studies of erect bipedalism which is a basic human action have been made, and technologies for supporting human walking and running more efficiently based on erect bipedalism mechanisms analyzed using biomechanics have been examined.

For example, JP 2012-501739T discloses an artificial foot and lower limb equipment or the like that supports human walking by applying torque to an ankle joint using an elastic member and a motor.

SUMMARY

Here, in the technology disclosed in JP 2012-501739T, torque is applied to an ankle joint from the elastic member when the angle between a lower limb or a foot part in the ankle joint is within a specific range. Accordingly, in the technology disclosed in JP 2012-501739T, when the angle between the lower limb and the foot part is within the above-mentioned range, torque may be applied in cases other than walking.

Thus, the present disclosure suggests a novel and improved movement support apparatus capable of switching transmission of a force from an elastic member to a joint part irrespective of an angle of a joint portion or a lower limb coupling portion coupled to a lower limb.

According to an embodiment of the present disclosure, there is provided a movement support apparatus including a lower limb coupling portion configured to be coupled to a lower limb, an elastic member, a ground contact unit configured to include a ground contact plate coming into contact with a surface and a transmission portion transmitting force generated by the elastic member, and an ankle portion configured to be installed between the lower limb coupling portion and the ground contact unit. The ground contact unit is installed to be displaceable between a position at which the transmission portion comes into contact with the ankle portion and a position at which the transmission portion is uncoupled from the ankle portion.

As described above, according to an embodiment of the present disclosure, it is possible to switch transmission of a force from the elastic member to the joint portion irrespective of an angle of the joint portion or the lower limb coupling portion coupled to a lower limb.

BRIEF DESCRIPTION OF THE DRAWINGS

FIG. 7A is an explanatory diagram illustrating an example of an operation of the movement support apparatus in step "A" according to the embodiment;

FIG. 7B is an explanatory diagram illustrating an example of an operation of the movement support apparatus in step "B" according to the embodiment;

FIG. 7C is an explanatory diagram illustrating an example of an operation of the movement support apparatus in step "C" according to the embodiment;

FIG. 7D is an explanatory diagram illustrating an example of an operation of the movement support apparatus in step "D" according to the embodiment;

FIG. 7E is an explanatory diagram illustrating an example of an operation of the movement support apparatus in step "E" according to the embodiment;

FIG. 7F is an explanatory diagram illustrating an example of an operation of the movement support apparatus in step "F" according to the embodiment;

DETAILED DESCRIPTION OF THE EMBODIMENTS

Figure 1:
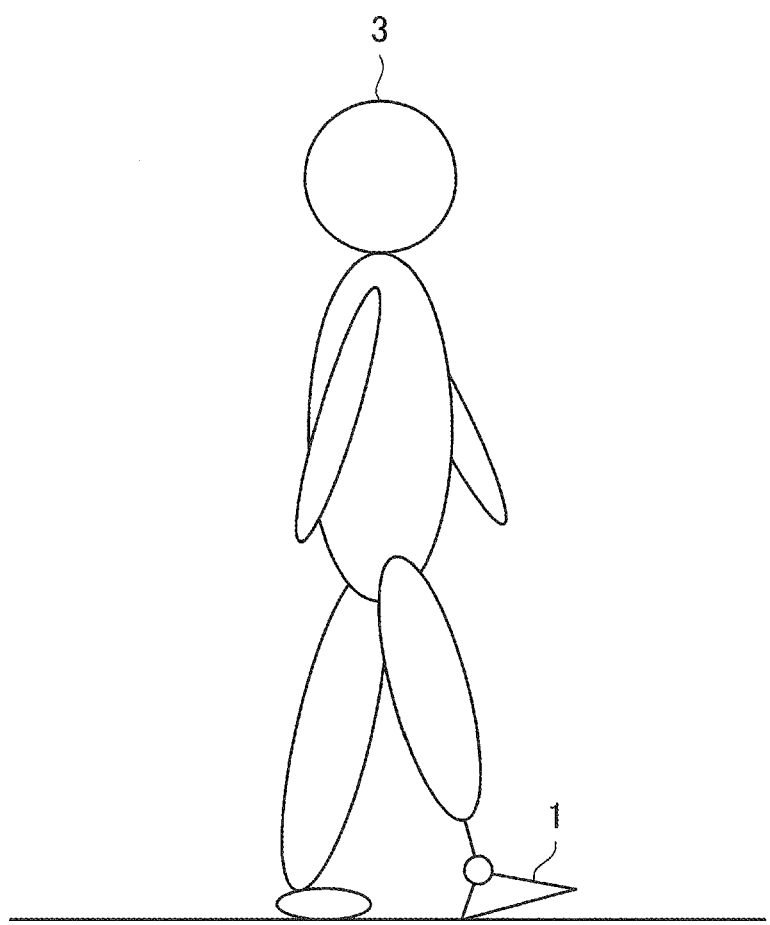
FIG. 1 is an explanatory diagram illustrating an application example of a movement support apparatus according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be made in the following order.
1. Overview of movement support apparatus
1.1 Application example of movement support apparatus
1.2 Operation overview of movement support apparatus
2. Specific configuration of movement support apparatus
2.1 Specific configuration of movement support apparatus 2.2 Functional configuration of movement support apparatus 3. Operation example of movement support apparatus
4. Advantage example of movement support apparatus
5. Conclusion <1. Overview of Movement Support Apparatus>

[1.1 Application Example of Movement Support Apparatus]

First, an overview of an embodiment of the present disclosure will be described with reference to FIG. 1. FIG. 1 is an explanatory diagram illustrating an application example of a movement support apparatus 1 according to the embodiment of the present disclosure.

As illustrated in FIG. 1, the movement support apparatus 1 according to the embodiment of the present disclosure is, for example, an artificial foot put on a user 3 whose lower limb has been amputated.

The movement support apparatus 1 supports movement of the user 3. Specifically, the movement support apparatus 1 is mounted on the lower limb of the user 3 to substitute for the amputated lower limb of the user 3 and reproduce walking and running functions. The movement support apparatus 1 according to the embodiment of the present disclosure can be particularly used properly for the user 3 of which a part including an ankle joint has been amputated since torque can be applied to the ankle joint by an elastic member or the like.

In the present specification, an example in which the movement support apparatus 1 according to the embodiment of the present disclosure is an artificial foot will be described, but embodiments of the present disclosure are not limited to the example. For example, the movement support apparatus 1 according to the embodiment of the present disclosure can also be used as movement support equipment put on a user whose walking ability is lowered due to aging, muscle weakness, or the like. For example, the movement support apparatus 1 according to the embodiment of the present disclosure can also be used as a movement apparatus included in a lower limb of a robot or the like performing bipedal walking.

[1.2 Operation Overview of Movement Support Apparatus]

Figure 2:
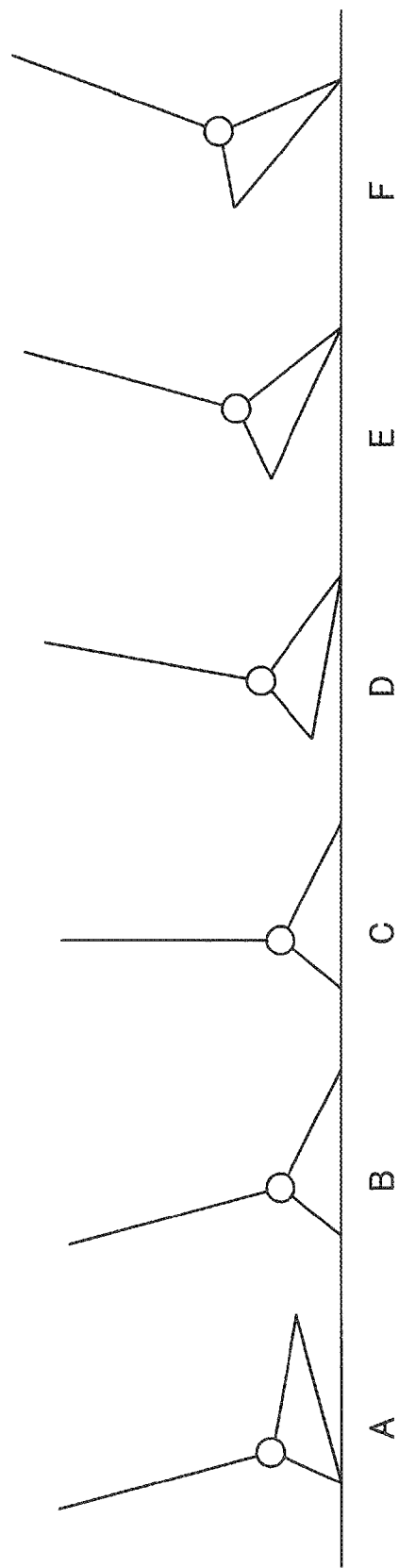
FIG. 2 is an explanatory diagram illustrating an operation of a lower limb when a human being is walking.
Figure 3:
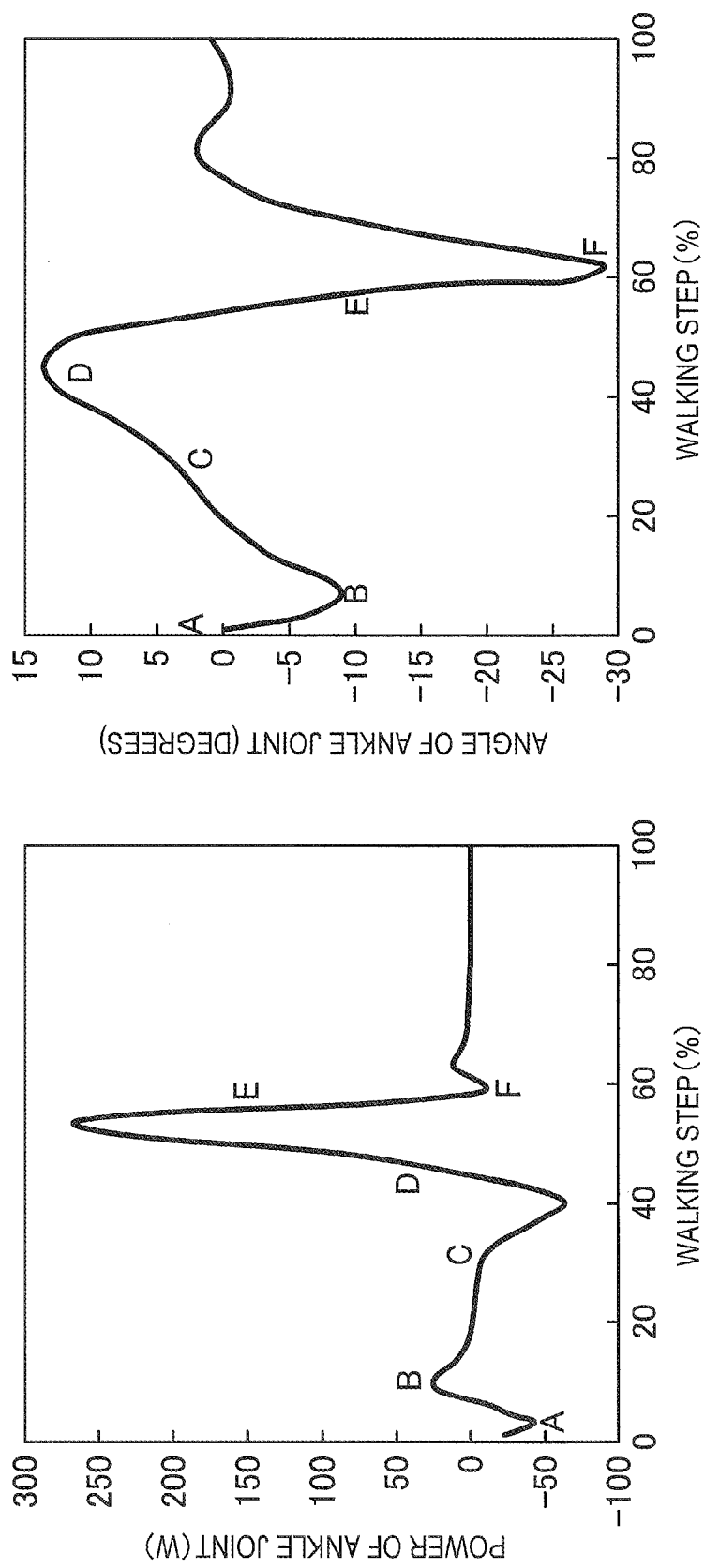
FIG. 3 is a graph diagram illustrating power (left drawing) output by an ankle joint at the time of walking at a movement speed of 1.25 m/s and an angle (right drawing) of the ankle joint.
Figure 4:
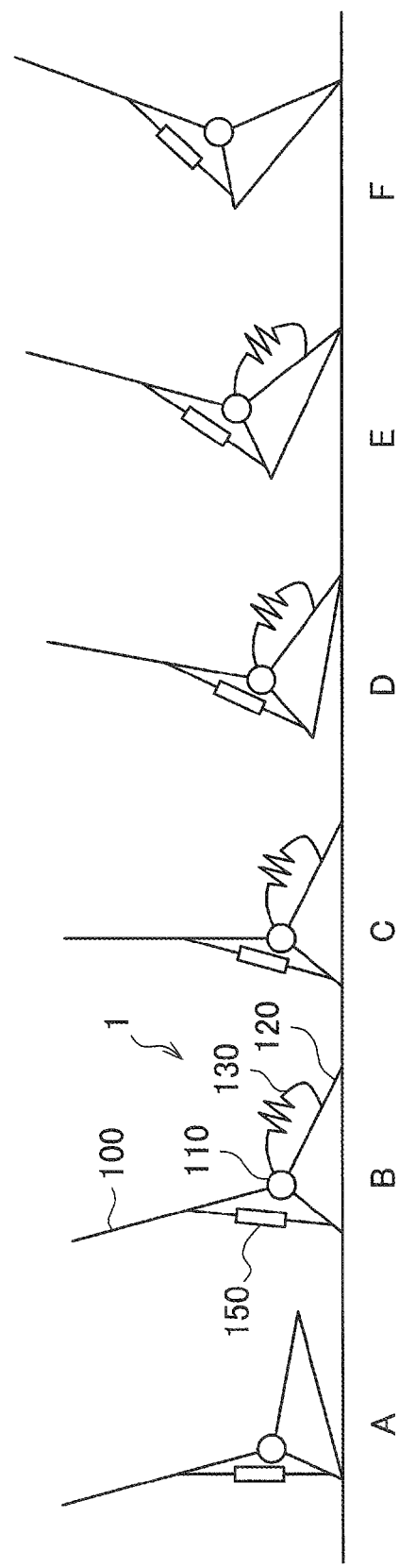
FIG. 4 is an explanatory diagram illustrating an overall operation of a movement support apparatus at the time of walking according to an embodiment of the present disclosure.

Next, an overview of an operation of the movement support apparatus 1 according to the embodiment of the present disclosure will be described with reference to FIGS. 2 to 4. FIG. 2 is an explanatory diagram illustrating an operation of a lower limb at the time of walking by a human being. FIG. 3 a graph diagram illustrating power (left drawing) output by an ankle joint and an angle (right drawing) of the ankle joint at a movement speed of 1.25 m/s. FIG. 4 is an explanatory diagram illustrating an overview of an operation at the time of walking of the movement support apparatus 1 according to the embodiment of the present disclosure.

First, the walking by a human being can be divided into a step in which a foot part does not come into contact with the ground surface and a step in which the foot part comes into contact with the ground surface. The step in which the foot part comes into contact with the ground surface is further divided into six steps "A" to "F," as illustrated in FIG. 2.

Specifically, the step in which the foot part comes into contact with the ground surface can be divided in to step "A" in which the heel comes into contact with the ground surface, step "B" in which the entire bottom surface of the foot part including the tip of the toe comes into contact with the ground surface, step "C" in which the same positional relation as that when the lower limb and the foot part are upright to the ankle joint is realized, step "D" in which the heel is uncoupled from the ground surface, step "E" in which the foot part is kicking the ground surface, and step "F" immediately before the tip of the toe is uncoupled from the ground surface. When the foot part uncoupled from the ground surface comes into contact with the ground surface from the heel again, the step returns to step "A."

Here, the power (left drawing) output by the ankle joint at the time of walking and the angle (right drawing) of the ankle joint at the time of walking will be described in correspondence with the above-described steps of the walking with reference to FIG. 3. In FIG. 3, corresponding positions of steps "A" to "F" of FIG. 2 in the graph of FIG. 3 are denoted with signs.

The left drawing of FIG. 3 shows the power output by the ankle joint at the time of walking and specifies that a direction (hereinafter referred to as a plantar flexion direction) in which the lower limb is bent toward an opposite side to the tip of the toe is positive and a direction (hereinafter referred to as a dorsiflexion direction) in which the lower limb is bent toward the toe tip side with respect to the foot part is negative. The right drawing of FIG. 3 shows a change in the angle of the ankle joint at the time of walking and specifies that a positional relation between the lower limb and the foot part at the time of erecting is 0°, a direction (hereinafter referred to as a dorsiflexion direction) in which the lower limb is bent toward the toe tip side with respect to the foot part is positive, and a direction (hereinafter referred to as a plantar flexion direction) in which the lower limb is bent toward the opposite side to the tip of the toe is negative.

As illustrated in the left drawing of FIG. 3, the maximum absolute value of the power output by the ankle joint at the time of walking from step "A" to step "C" is 50 W. On the other hand, it is necessary for the ankle joint to output the absolute value of power of 250 W or more through step "D" and step "E" in which an operation in which the foot part kicks the ground surface is performed.

Accordingly, for example, when the power output by the ankle joint described above is substituted using a motor, it is necessary to use the motor capable of outputting the power necessary at step "D" and step "E." However, since a motor having large output power has a large size, the motor is heavy. For this reason, mounting a movement support apparatus including a motor having the large output considerably burdens the user 3.

As illustrated in the right drawing of FIG. 3, the angle of the ankle joint at step "A" is 0° and the angle of the ankle joint is negative (on the plantar flexion side) from step "B" to step "C." Since the ankle joint is rotated with weight shift in the dorsiflexion direction from step "C" to step "D," the angle of the ankle joint is positive (on the dorsiflexion side). Thereafter, since the ankle joint is rotated with the kicking of the ground surface in the plantar direction from step "D" to step "F," the angle of the ankle joint is changed from the positive value (dorsiflexion side) to the negative value (plantar flexion side). Thus, in step "D" and step "E" in which it is necessary for the ankle joint to output the maximum power, the angle of the ankle joint becomes negative (the plantar flexion side) for a part of the steps.

Here, in the technology disclosed in JP 2012-501739T, torque is applied to the ankle joint from the elastic member when the angle of the ankle joint is positive (on the dorsiflexion side). Accordingly, in the technology disclosed in JP 2012-501739T, when the maximum power is output by the ankle joint, it is difficult to apply torque from the elastic member to the ankle joint, and thus movement support for the user 3 may not be performed properly in some cases. Further, in the technology disclosed in JP 2012-501739T, since it is necessary to use a motor capable of outputting the maximum power necessary for the ankle joint in step "D" and step "E," it is necessary to use a motor with a large size and a heavy weight.

Accordingly, as the result of the thorough repeated examinations on the movement support apparatuses, the inventors of the present disclosure have devised the movement support apparatus 1 according to the embodiment of the present disclosure to resolve the above-mentioned matters. The movement support apparatus 1 according to the embodiment of the present disclosure is capable of transmitting force from an elastic member to an ankle joint when the ankle joint outputs the maximum power irrespective of an angle of the ankle joint.

Hereinafter, an overall operation of the movement support apparatus 1 according to the embodiment of the present disclosure will be described schematically with reference to FIG. 4. FIG. 4 is an explanatory diagram schematically illustrating the overall operation of the movement support apparatus 1 according to the embodiment of the present disclosure. Further, step "A" to step "F" in FIG. 4 correspond to step "A" to step "F" described in FIG. 2, respectively.

As illustrated in FIG. 4, for example, the movement support apparatus 1 according to the embodiment of the present disclosure includes a lower limb coupling portion 100, an ankle portion 110, a ground contact unit 120, an elastic member 130, and a motor 150. With progress of walking steps, coupling between the elastic member 130 and the ankle portion 110 is switched.

In FIG. 4, coupling and non-coupling between the elastic member 130 and the ankle portion 110 are expressed by presence and absence of the illustration of the elastic member 130. Specifically, in step "A" and step "F" in which the elastic member 130 is not illustrated, the coupling between the elastic member 130 and the ankle portion 110 is not made. Further, in step "B" to step "E" in which the elastic member 130 is illustrated, the coupling between the elastic member 130 and the ankle portion 110 is made, and thus force transmission is possible.

Here, the lower limb coupling portion 100 is a portion coupled to a lower limb of the user 3 and the ankle portion 110 is a portion corresponding to an ankle part of a human being. The ground contact unit 120 is a portion corresponding to a foot part of a human being. The elastic member 130 and the motor 150 apply torque to the ankle portion 110.

As illustrated in FIG. 4, the elastic member 130 is not coupled to the ankle portion 110 in step "A" in which the heel comes into contact the ground surface. Next, in step "B," the elastic member 130 is coupled to the ankle portion 110 when the entire ground contact unit 120 including the toe tip side comes into contact with the ground surface.

Subsequently, throughout step "B" to step "D," the elastic member 130 accumulates elastic energy while the angle of the ankle portion 110 is rotated in the dorsiflexion direction. Throughout step "D" to step "E," the elastic member 130 applies the accumulated elastic energy as torque to the ankle portion 110 to reduce a load of the motor 150. Further, in step "F," the elastic member 130 releases the coupling with the ankle portion 110 when the tip of the toe is uncoupled from the ground surface.

As described above, in the movement support apparatus 1 according to the embodiment of the present disclosure, the coupling between the elastic member 130 and the ankle portion 110 is switched based on ground contact of the entire ground contact unit 120. Accordingly, in the movement support apparatus 1 according to the embodiment of the present disclosure, the torque can be applied from the elastic member 130 to the ankle portion 110 in step "D" and step "E" in which the maximum power is necessary in the ankle portion 110.

In the above configuration, even when the motor 150 is used, the maximum output of the motor 150 can be reduced, thereby reducing the size and the weight of the motor 150. Accordingly, the movement support apparatus 1 according to the embodiment of the present disclosure can reduce a load of the user 3. Further, since the movement support apparatus 1 is reduced in size and weight, the application range of the movement support apparatus 1 can be increased even for the user 3 who has had a small part amputated.

<2. Specific Configuration of Movement Support Apparatus>

[2.1 Specific Configuration of Movement Support Apparatus]

Figure 5:
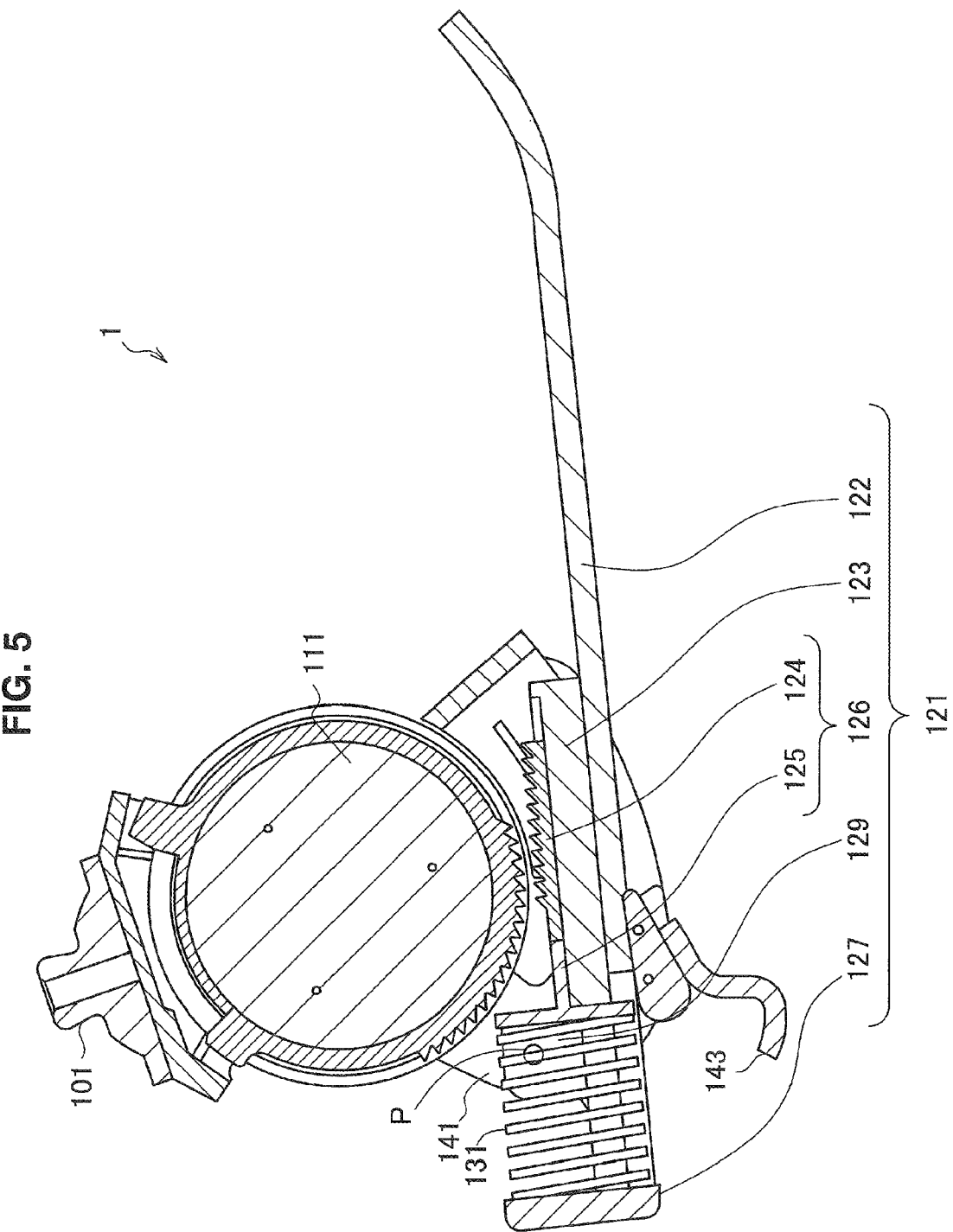
FIG. 5 is an explanatory diagram illustrating the cross-sectional configuration of the movement support apparatus according to the embodiment.

Next, a specific configuration of the movement support apparatus 1 according to the embodiment of the present disclosure will be described with reference to FIG. 5. FIG. 5 is an explanatory diagram illustrating the cross-sectional configuration of the movement support apparatus 1 according to the embodiment of the present disclosure.

As illustrated in FIG. 5, the movement support apparatus 1 according to the embodiment of the present disclosure includes a lower limb coupling portion 101, an ankle portion 111, a ground contact unit 121, an elastic member 131, a coupling plate 141, and a heel-side ground contact plate 143. The ground contact unit 121 includes a ground contact plate 122, a slider plate 123, a transmission portion 126 including an ankle-side transmission portion 124 and an elastic-member-side transmission portion 125, an abutting portion 127, and a ground-contact unit coupling plate 129.

One side of the lower limb coupling portion 101 is coupled to a lower limb of the user 3 and the other side thereof is coupled to the ankle portion 111. Accordingly, the lower limb coupling portion 101 can couple the lower limb of the user 3 coupled via another artificial foot part, an adapter, or the like to the ankle portion 111 and the ground contact unit 121.

The ankle portion 111 is installed between the lower limb coupling portion 101 and the ground contact unit 121. The ankle portion 111 has a circular shape on the plane perpendicular to the ground surface and including a movement direction of the user 3 and a rotational mechanism that is rotatable around an axis perpendicular to the plane. The ankle portion 111 can rotate the coupled lower limb coupling portion 101 by the rotational mechanism.

The ankle portion 111 includes a motor (not illustrated) applying torque to the rotational mechanism to which the above-described lower limb coupling portion 101 is coupled. The ankle portion 111 can apply torque when the lower limb coupling portion 101 is rotated by the included motor. The ankle portion 111 may include a Harmonic Drive (registered trademark) which is strain wave gearing to amplify torque to be applied. A method of controlling an output of the motor will be described below.

Here, a part of the outer edge of the ankle portion 111 is formed in a shape engaging with the ankle-side transmission portion 124. Specifically, the part of the outer edge of the ankle portion 111 is formed with a pinion gear shape engaging with a rack gear included in the ankle-side transmission portion 124. Accordingly, when the ankle portion 111 comes into contact with the transmission portion 126, the ankle portion 111 engages with the rack gear shape of the transmission portion 126, so that force can be transmitted from the transmission portion 126. The ankle portion 111 and the ankle-side transmission portion 124 can convert force of a linear direction from the elastic member 131 into force of a rotational direction and apply the force to the ankle portion 111 using the rack-and-pinion mechanism for the force transmission.

The ground contact plate 122 is formed with a plate shape that extends when the movement direction of the user 3 is a longitudinal direction and with a shape of which one end on the toe tip side is gently curved in the thickness direction. The ground contact plate 122 comes into contact with the ground surface on the toe tip side curved in the thickness direction and is coupled to the coupling plate 141 through the ground-contact unit coupling plate 129 having a coupling point P on the opposite side to the ground contact side and the position at which the slider plate 123 is installed. Since the ground contact plate 122 is a member supporting the weight of the user 3 and coming into contact with the ground surface, the ground contact plate 122 is preferably formed of, for example, a material having a high strength that is not easily corroded, such as carbon fiber reinforced plastic.

The slider plate 123 is a linear slider having a slider groove and is formed on the ground contact plate 122. The ankle-side transmission portion 124 is installed above the slider plate 123 and the ankle-side transmission portion 124 slides along the slider groove on the slider plate 123.

The slider plate 123 is formed to be longer than the combined length of the ankle-side transmission portion 124 and the elastic-member-side transmission portion 125, and thus a surplus portion is formed at one end opposite to the elastic-member-side transmission portion 125. In such a configuration, the slider plate 123 can slide the ankle-side transmission portion 124 to the opposite side to the elastic-member-side transmission portion 125 when the movement support apparatus 1 kicks the ground surface, thereby performing kicking the ground surface more smoothly.

The transmission portion 126 includes the ankle-side transmission portion 124 formed on the slider plate 123 and the elastic-member-side transmission portion 125 coming into contact with the elastic member 131. The ankle-side transmission portion 124 and the elastic-member-side transmission portion 125 are separated from each other and are coupled by a coupling part with elasticity. In such a configuration, the ankle-side transmission portion 124 and the elastic-member-side transmission portion 125 can be isolated from each other when external force is applied, and can return to the contact state when no external force is applied.

The ankle-side transmission portion 124 is formed in a rack gear shape engaging with the pinion gear formed in the part of the outer edge of the ankle portion 111. In such a configuration, when the ankle-side transmission portion 124 comes into contact with the ankle portion 111, the shape of the ankle-side transmission portion 124 can engage with the shape of the ankle portion 111. Thus, the force from the elastic member 131 can be transmitted to the ankle portion 111.

The elastic-member-side transmission portion 125 is installed between and comes into contact with both of the ankle-side transmission portion 124 and the elastic member 131. In such a configuration, the elastic-member-side transmission portion 125 can transmit the force from the elastic member 131 to the ankle-side transmission portion 124. The elastic-member-side transmission portion 125 can be slid on the slider plate 123 to the side of the elastic member 131 to elastically deform the elastic member 131.

The abutting portion 127 is installed to be fixed to the coupling plate 141 on the opposite side to the elastic-member-side transmission portion 125 with respect to the elastic member 131. Accordingly, when the elastic-member-side transmission portion 125 is slid to the side of the abutting portion 127, the abutting portion 127 can compress the elastic member 131 between the abutting portion 127 and the elastic-member-side transmission portion 125 to elastically deform the elastic member 131.

The ground-contact unit coupling plate 129 is installed to have the coupling point P on both sides of the ground contact plate 122. The ground-contact unit coupling plate 129 couples the ground contact unit 121, which includes the ground contact plate 122, the slider plate 123, the transmission portion 126, and the abutting portion 127, to the coupling plate 141 at the coupling point P. In such a configuration, the ground-contact unit coupling plate 129 can displace the ground contact unit 121 around the coupling point P between a position at which the transmission portion 126 comes into contact with the ankle portion 111 and a position at which the transmission portion 126 and the ankle portion 111 are isolated from each other.

Here, the coupling point P is installed such that the ground contact side of the ground contact plate 122 and the transmission portion 126 are present on the same side with respect to the coupling point P. In such a configuration, when the ground contact unit 121 is displaced around the coupling point P, the displacement direction of the ground contact side of the ground contact plate 122 and the displacement direction of the transmission portion 126 are identical. Accordingly, when the ground contact plate 122 comes into contact with the ground surface, the ground contact plate 122 is displaced upward due to the reactive force from the ground surface and the transmission portion 126 is also displaced upward. At this time, since the upward displaced transmission portion 126 comes into contact with the ankle portion 111, force can be transmitted from the elastic member 131 to the ankle portion 111. Accordingly, the movement support apparatus 1 can switch the coupling of the elastic member 131 and the ankle portion 111 irrespective of the angle of the lower limb coupling portion 101 and the ankle portion 111.

The elastic member 131 is installed between the elastic-member-side transmission portion 125 and the abutting portion 127. When the transmission portion 126 and the ankle portion 111 come into contact with each other, the elastic member 131 is compressed to be elastically deformed by the fixed abutting portion 127 and the elastic-member-side transmission portion 125 slid with the rotation of the ankle portion 111. In such a configuration, the elastic member 131 applies the repulsive force at the time of the elastic deformation to the ankle portion 111 through the transmission portion 126. Here, for example, the elastic member 131 may be a coil spring or may be a plate spring, a tension spring, an air spring, or the like.

The coupling plate 141 is formed in substantially an "L" plate shape and is installed between both sides of the ankle portion 111, the ground-contact unit coupling plate 129, and the heel-side ground contact plate 143. The ankle portion 111, the ground-contact unit coupling plate 129 of the ground contact unit 121, and the heel-side ground contact plate 143 are interposed between the two coupling plates 141 with the same shape, so that the coupling plates 141 couples them to each other. In FIG. 5, the coupling plate 141 present on the closer side is not illustrated to clarify the configuration.

The heel-side ground contact plate 143 is formed on the heel side which is the rear side in the movement direction of the user 3. The heel-side ground contact plate 143 comes into contact with the ground surface to support the weight of the user 3. The heel-side ground contact plate 143 comes into contact with the ground contact unit 121 displaced downward due to its weight around the coupling point P to support the ground contact unit 121. Here, since the heel-side ground contact plate 143 is a member supporting the weight of the user 3 and coming into contact with the ground surface, as in the ground contact plate 122, the heel-side ground contact plate 143 is preferably formed of, for example, a material having a high strength that is not easily corroded, such as carbon fiber reinforced plastic.

In the above-described embodiment, the example in which the elastic member 131 is installed on the heel side below the ankle portion 111 has been described. However, embodiments of the present disclosure are not limited to the position of the elastic member 131 illustrated in FIG. 5. For example, the elastic member 131 may be a tension spring installed on the heel side with respect to the ankle portion 111. Further, the elastic member 131 may be installed on the heel side so that the extension direction is vertical. Embodiments of the present disclosure are not limited by a type, an installation position, and an installation direction of the elastic member.

In the above-described embodiment, the example in which the elastic member 131 and the ground contact unit 121 are separately configured has been described, but embodiments of the present disclosure are not limited to the example. The elastic member 131 may include the ground contact unit 121.

[2.2 Functional Configuration of Movement Support Apparatus]

Figure 6:
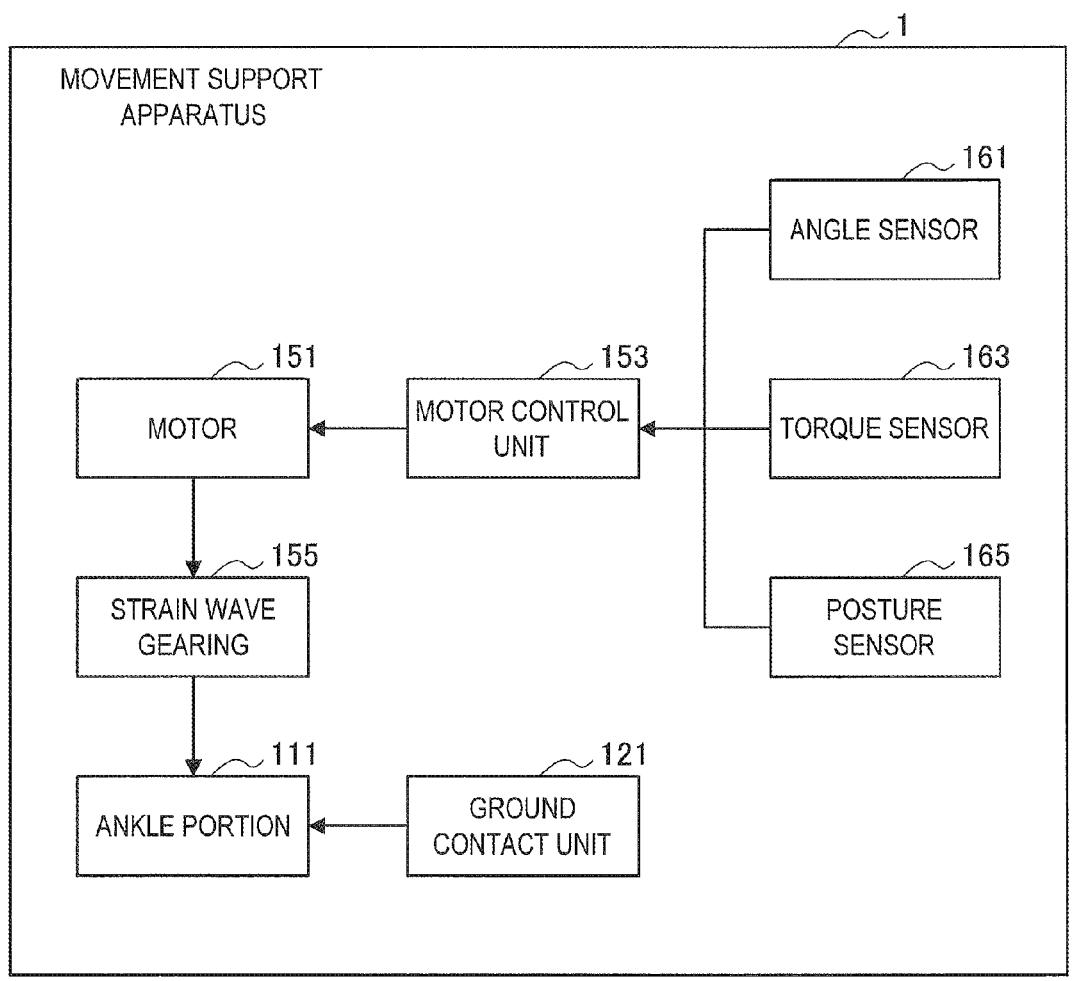
FIG. 6 is a block diagram illustrating the functional configurations of the movement support apparatus according to the embodiment.

Next, the functional configuration of the movement support apparatus 1 according to the embodiment of the present disclosure will be described with reference to FIG. 6. FIG. 6 is a block diagram illustrating the functional configuration of the movement support apparatus 1 according to the embodiment of the present disclosure.

As illustrated in FIG. 6, the movement support apparatus 1 according to the embodiment of the present disclosure includes an angle sensor 161, a torque sensor 163, a posture sensor 165, a motor control unit 153, a motor 151, strain wave gearing 155, an ankle portion 111, and a ground contact unit 121. Here, since the ground contact unit 121 and the ankle portion 111 are the same as those described with reference to FIG. 5, the detailed description will be omitted herein.

The angle sensor 161 measures an angle of an ankle joint. Specifically, for example, the angle sensor 161 measures the angle of the ankle joint by measuring an angle of the ground contact unit 121 with respect to the lower limb coupling portion 101 or measuring a rotation angle or the like of the ankle portion 111. For example, the angle sensor 161 may be a sensor including a resolver, a rotary encoder, or a potentiometer.

The torque sensor 163 measures torque applied to the ankle portion 111. Specifically, the torque sensor 163 measures a sum value of torque applied from the motor 151 and the elastic member 131 to the ankle portion 111. For example, the torque sensor 163 may be a sensor including a distortion gauge or a piezoelectric element.

The posture sensor 165 measures an inclination of the ankle portion 111 in a space. Specifically, the posture sensor 165 measures an inclination of the ankle portion 111 in the vertical direction and the horizontal direction in a space. For example, the posture sensor 165 may be a sensor including a gyroscope.

The motor control unit 153 controls an output of the motor 151 based on information from various sensors. Specifically, the motor control unit 153 controls an output of the motor 151 based on information measured by the angle sensor 161, the torque sensor 163, and the posture sensor 165 and controls torque applied to the ankle portion 111. The motor control unit 153 may calculate a movement speed based on information measured by the angle sensor 161 and the torque sensor 163 and control an output of the motor 151 based on the movement speed.

The motor control unit 153 may be configured to include a central processing unit (CPU) which is an arithmetic processing device, a read-only memory (ROM) storing arithmetic parameters, a program, and the like used by the CPU, and a random access memory (RAM) temporarily storing a program used in execution of the CPU, parameters properly changed in the execution, and the like.

The motor 151 generates torque and applies the torque to the ankle portion 111. The strain wave gearing 155 is, for example, a decelerator called a Harmonic Drive (registered trademark) and amplifies the torque output by the motor 151. Specifically, the torque output by the motor 151 is amplified by the strain wave gearing 155 and is applied to the ankle portion 111.

For example, the rotation of the motor 151 may be converted in a linear direction by a ball screw or the like, may be converted into an elastic force of a coil spring or the like, and may be applied to the ankle portion 111. However, when the strain wave gearing 155 is used, the size and the weight of a mechanism applying torque from the motor 151 or the like to the ankle portion 111 can be reduced. Accordingly, to reduce the burden on the user 3, it is more preferable to use the strain wave gearing 155. In such a configuration, since the movement support apparatus 1 can be reduced, an application range of the movement support apparatus 1 according to the embodiment of the present disclosure can be increased even for the user who has had a small part amputated.

Torque is applied to the ankle portion 111 by the motor 151 and the ground contact unit 121. Here, the ground contact unit 121 may include the elastic member 131, whether the torque from the elastic member 131 is applied to the ankle portion 111 is switched depending on whether the transmission portion 126 comes into contact with the ankle portion 111.

<3. Operation Example of Movement Support Apparatus>

Next, examples of operations of the movement support apparatus 1 according to the embodiment of the present disclosure will be described with reference to FIGS. 7A to 7F. FIGS. 7A to 7F are explanatory diagrams illustrating examples of operations of the movement support apparatus 1 at the walking steps (step "A" to step "F") according to the embodiment of the present disclosure. Here, since the reference numerals given in the movement support apparatus 1 and constituent elements in FIGS. 7A to 7F are the same as the reference numerals given to the constituent elements described with reference to FIG. 5 and description thereof is the same, the description will be omitted herein.

Further, step "A" of the walking described in FIG. 2 or 4 corresponds to FIG. 7A. Likewise, step "B" corresponds to FIG. 7B, step "C" corresponds to FIG. 7C, step "D" corresponds to FIG. 7D, step "E" corresponds to FIG. 7E, and step "F" corresponds to FIG. 7F.

As illustrated in FIG. 7A, first, the heel-side ground contact plate 143 comes into contact with the ground surface in step "A." At this time, the ankle-side transmission portion 124 and the ankle portion 111 do not come into contact with each other so and a gap is empty. Then, the ground contact plate 122 is displaced downward due to its weight around the coupling point P to come into contact with the heel-side ground contact plate 143. In the initial state, the elastic member 131 has a natural length.

Next, as illustrated in FIG. 7B, the ground contact plate 122 comes into contact with the ground surface in step "B." When the ground contact plate 122 comes into contact with the ground surface, the ground contact plate 122 is displaced upward around the coupling point P due to the reactive force from the ground surface. Accordingly, the slider plate 123 and the ankle-side transmission portion 124 installed on the ground contact plate 122 are likewise displaced upward, so that the ankle-side transmission portion 124 comes into contact with the ankle portion 111.

Here, since the outer edge of the ankle portion 111 and the ankle-side transmission portion 124 are a rack-and-pinion mechanism having the engaging shape, the force can be transmitted as the shapes thereof engage with each other. Further, since the ground contact plate 122 is displaced upward around the coupling point P, the gap between the ground contact plate 122 and the heel-side ground contact plate 143 is empty.

Subsequently, as illustrated in FIG. 7C, the lower limb coupling portion 101 and the ankle portion 111 are rotated in the dorsiflexion direction in step "C" more than at the position of step "B." Since the ankle-side transmission portion 124 has the shape engaging with the ankle portion 111, the ankle-side transmission portion 124 is slid on the slider plate 123 with the rotation of the ankle portion 111 to move the elastic-member-side transmission portion 125 to the side of the abutting portion 127. Accordingly, the elastic member 131 is compressed between the elastic-member-side transmission portion 125 and the abutting portion 127 to apply the repulsive force to the ankle portion 111 and accumulate elastic energy by the elastic deformation.

Next, as illustrated in FIG. 7D, the heel-side ground contact plate 143 becomes uncoupled from the ground surface in step "D." At this time, since the lower limb coupling portion 101 and the ankle portion 111 are further rotated in the dorsiflexion direction, the elastic member 131 is further elastically deformed by the ankle-side transmission portion 124 and the elastic-member-side transmission portion 125 to apply the repulsive force to the ankle portion 111. In this step, the heel-side ground contact plate 143 is uncoupled from the ground surface. However, since the side of the tip of the toe of the ground contact plate 122 comes into contact with the ground surface and receives the reactive force from the ground surface, the contact between the ankle portion 111 and the ankle-side transmission portion 124 is not released.

Subsequently, as illustrated in FIG. 7E, kicking the ground surface is performed by the ground contact plate 122 in step "E." At this time, the rotation direction of the ankle portion 111 is changed to the plantar flexion direction after step "D." Accordingly, the elastic energy accumulated in the elastic member 131 from step "B" to step "D" is applied as the repulsive force of the elastic member 131 to the ankle portion 111 after step "D." In such a configuration, as described with reference to the right drawing of FIG. 3, the elastic member 131 can apply the repulsive force to the ankle portion 111 through step "D" and step "E" in which power is most necessary in the ankle portion 111. When the motor 151 is used, the maximum value of the motor output can be reduced.

Further, as illustrated in FIG. 7F, the kicking on the ground surface by the ground contact plate 122 is completed in step "F." At this time, the ankle portion 111 is rotated in the plantar flexion direction more than in step "E" and the ankle-side transmission portion 124 becomes uncoupled from the elastic-member-side transmission portion 125 with the rotation of the ankle portion 111.

Here, when the elastic-member-side transmission portion 125 and the ankle-side transmission portion 124 are integrally formed and the length of the elastic member 131 returns to the natural length in FIG. 7E and the like, the ankle-side transmission portion 124 is not able to be further moved to the side of the tip of the toe. In this case, since the ankle portion 111 engages with the ankle-side transmission portion 124, the ankle portion 111 is not able to be further rotated in the plantar flexion direction, thereby obstructing natural kicking of the user 3.

In the movement support apparatus 1 according to the embodiment of the present disclosure, the ankle-side transmission portion 124 and the elastic-member-side transmission portion 125 are configured to be separated from each other. Accordingly, even when the length of the elastic member 131 returns to the natural length in FIG. 7E and the like, the ankle-side transmission portion 124 can be separated from the elastic-member-side transmission portion 125 to be moved. Accordingly, the ankle-side transmission portion 124 does not obstruct the rotation of the ankle portion 111 and the user 3 can perform natural kicking.

Although not illustrated, when the ground contact plate 122 becomes away from the ground surface in step "F," the reactive force received from the ground surface by the ground contact plate 122 disappears, and thus the ground contact unit 121 is displaced downward around the coupling point P. Therefore, the contact between the ankle portion 111 and the ankle-side transmission portion 124 is released. Here, since the ankle-side transmission portion 124 and the elastic-member-side transmission portion 125 are coupled to each other by the coupling part with elasticity, the ankle-side transmission portion 124 returns to the contact position with the elastic-member-side transmission portion 125 by the elastic force of the coupling part with the releasing of the contact. In such a configuration, when the movement support apparatus 1 comes into contact with the ground surface again, the operation returns to step "A" and the same operation can be repeated.

Due to the above-described operations, the movement support apparatus 1 according to the embodiment of the present disclosure brings the transmission portion 126 into contact with the ankle portion 111 to transmit the force from the elastic member 131 to the ankle portion 111 when the ground contact plate 122 comes into contact with the ground surface. When the ground contact plate 122 moves away from the ground surface, the movement support apparatus 1 releases the transmission of the force from the elastic member 131 to the ankle portion 111 by releasing the contact between the transmission portion 126 and the ankle portion 111. Accordingly, the movement support apparatus 1 according to the embodiment of the present disclosure can apply the force from the elastic member 131 to the ankle portion 111 in step "D" and step "E" in which power is most necessary in the ankle portion 111.

<4. Advantage Example of Movement Support Apparatus>

Figure 8A:
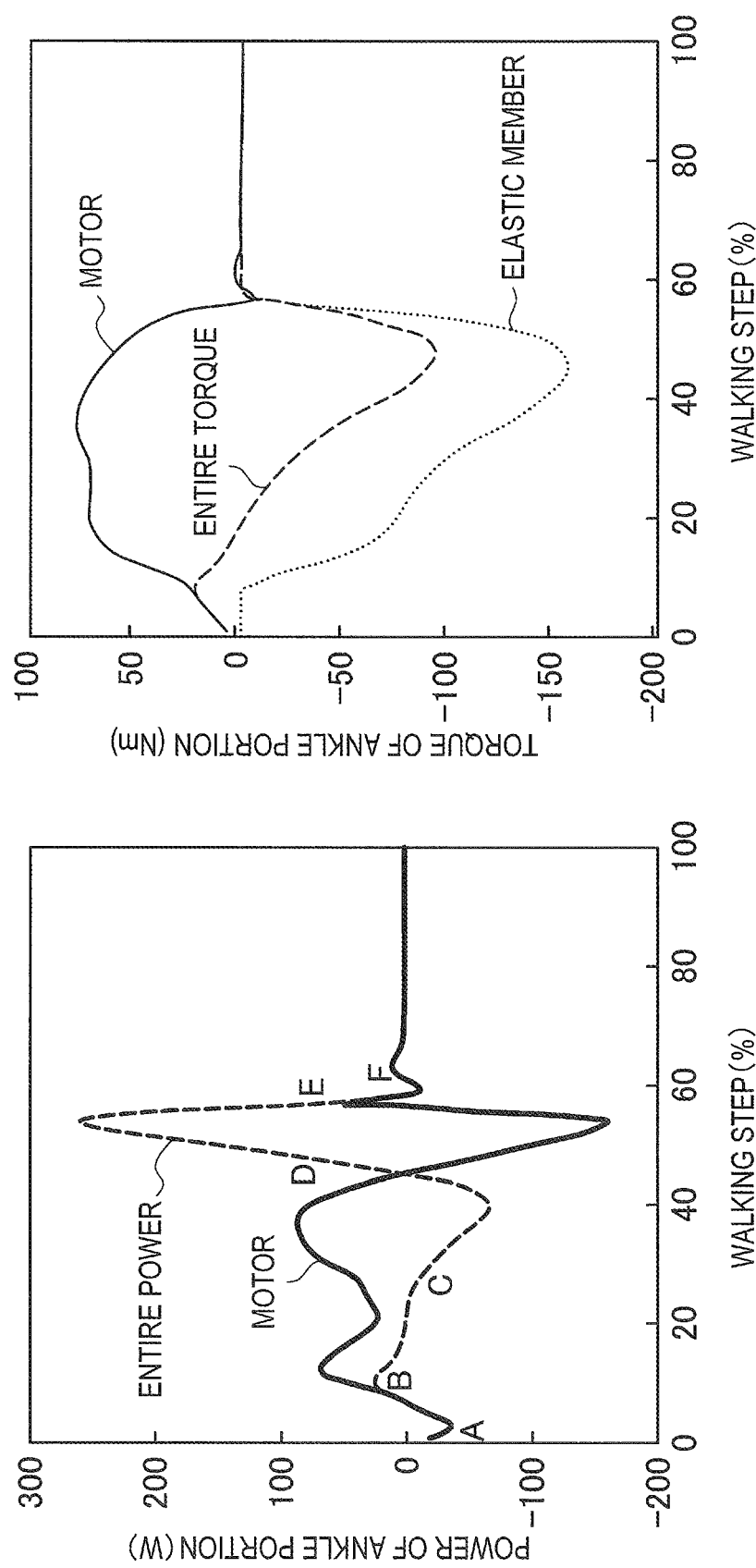
FIG. 8A is a graph diagram illustrating power (left drawing) output by an ankle portion of the movement support apparatus at a movement speed of 1.25 m/s and torque (right drawing) applied by an elastic member and a motor according to the embodiment.
Figure 8B:
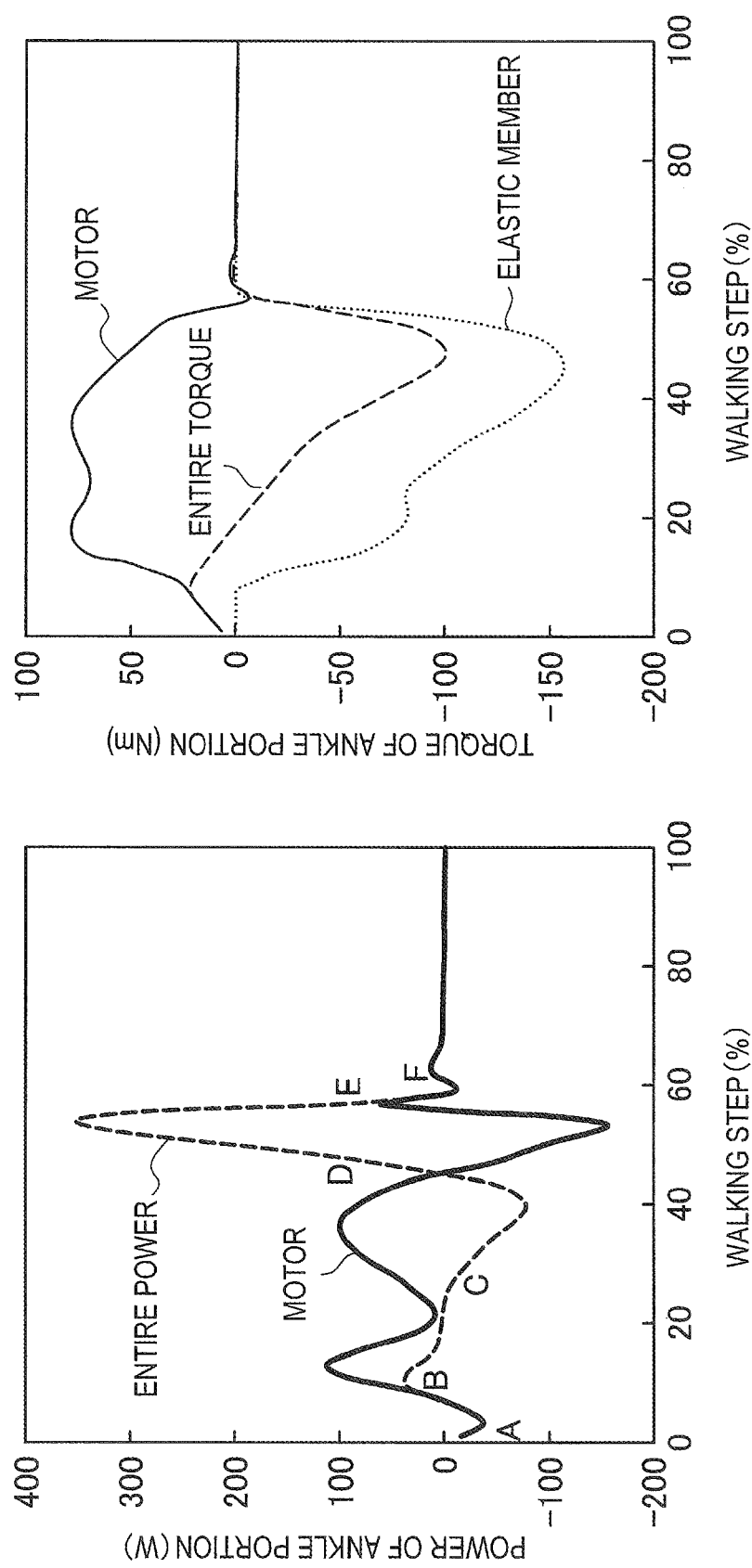
FIG. 8B is a graph diagram illustrating power (left drawing) output by the ankle portion of the movement support apparatus at a movement speed of 1.50 m/s and torque (right drawing) applied by the elastic member and the motor according to the embodiment.

Advantage examples of the movement support apparatus 1 according to the embodiment of the present disclosure will be described with reference to FIGS. 8A to 8C. FIG. 8A is a graph diagram illustrating power (left drawing) output by the ankle portion 111 of the movement support apparatus 1 at a movement speed of 1.25 m/s and torque (right drawing) applied by the elastic member 131 and the motor 151. FIG. 8B is a graph diagram illustrating the same parameters as those of FIG. 8A at a movement speed of 1.50 m/s and FIG.

8C is a graph diagram illustrating the same parameters as those of FIG. 8A at a movement speed of 1.75 m/s.

Figure 8C:
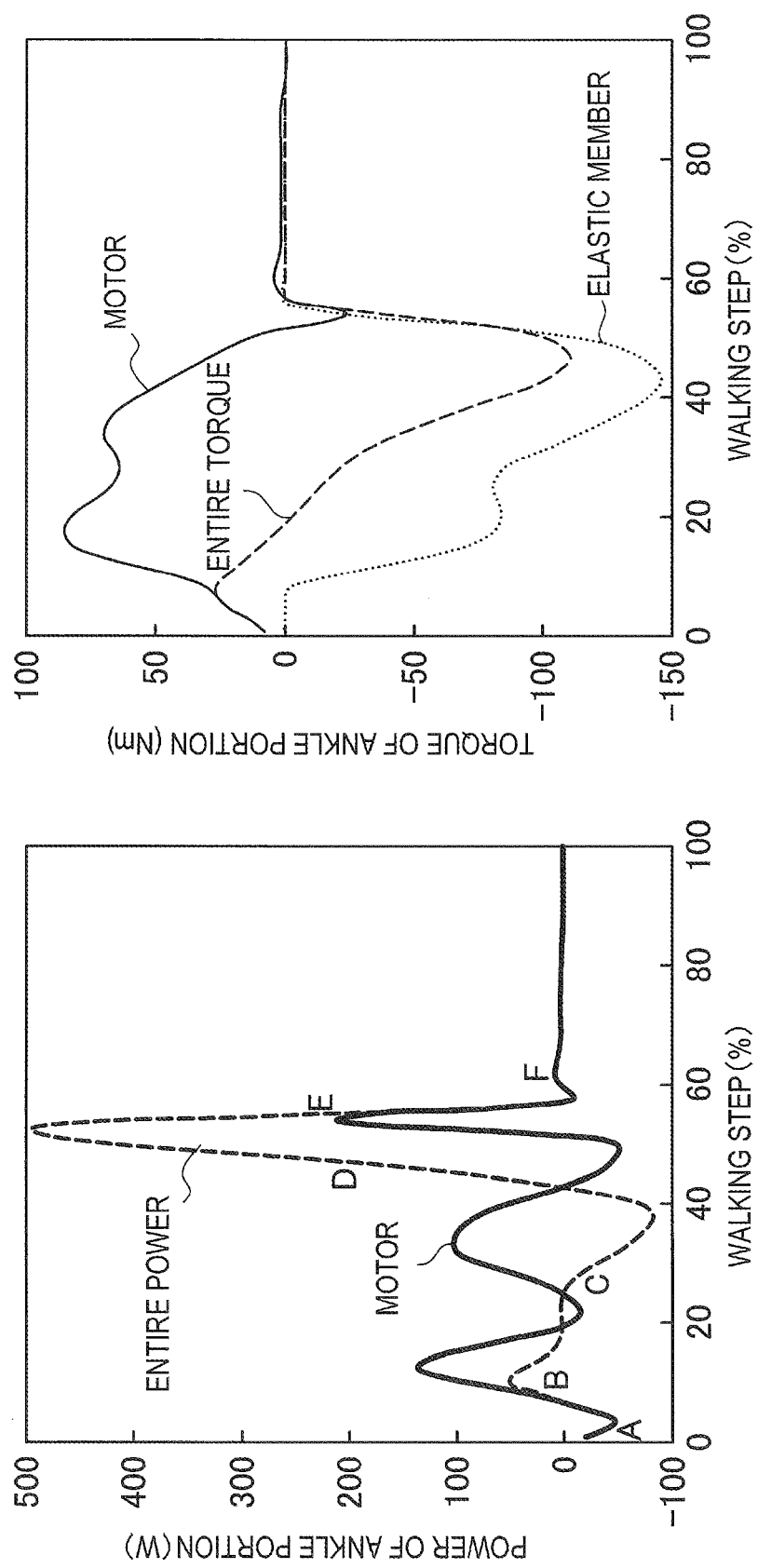
FIG. 8C is a graph diagram illustrating power (left drawing) output by the ankle portion of the movement support apparatus at a movement speed of 1.75 m/s and torque (right drawing) applied by the elastic member and the motor according to the embodiment.

Here, in the left diagram of each of FIGS. 8A to 8C, power output by the motor 151 is indicated by a solid line and power output by the entire ankle portion 111 is indicated by a dashed line. In the right drawing of each of FIGS. 8A to 8C, torque applied by the motor 151 is indicated by a solid line, torque applied by the elastic member 131 is indicated by a dotted line, and torque applied to the entire ankle portion 111, which is a sum of the torque applied by the motor 151 and the torque applied by the elastic member 131, is indicated by a dashed line. In the left drawing of each of FIGS. 8A to 8C, the plantar flexion direction is assumed to be positive and the dorsiflexion direction is assumed to be negative, as in the left drawing of FIG. 3. In the right drawing of each of FIGS. 8A to 8C, the dorsiflexion direction is assumed to be positive and the plantar flexion direction is assumed to be negative.

As illustrated in the left drawing of each of FIGS. 8A to 8C, the maximum value of the absolute value of the power output by the entire ankle portion 111 increases as the movement speed is faster. Specifically, in step "D" and step "E," the absolute value of the power output by the entire ankle portion 111 is 250 W at the movement speed of 1.25 m/s, as illustrated in FIG. 8A, is 350 W at the movement speed of 1.50 m/s, as illustrated in FIG. 8B, and is 500 W at the movement speed of 1.75 m/s, as illustrated in FIG. 8C. However, the power output by the motor 151 is different from the power output by the entire ankle portion 111 and the absolute value thereof converges at substantially 150 W regardless of the movement speed. This is because in the movement support apparatus 1 according to the embodiment of the present disclosure, the torque is applied to the ankle portion 111 by the elastic member 131 so that the power output to the ankle portion 111 by the motor 151 is not increased even in step "D" and step "E."

Here, in the advantage examples illustrated in FIGS. 8A to 8C, as illustrated in the right drawing of each of FIGS. 8A to 8C, the elastic force (for example, a spring constant) of the elastic member 131 is determined so that the torque applied by the elastic member 131 is greater than the torque applied to the entire ankle portion 111. Therefore, a force direction (that is, the sign of the graph) of the torque applied to the ankle portion 111 by the motor 151 is an opposite direction to that of the torque applied by the elastic member 131. In particular, in step "D" and step "E" in which the movement speed is slow in the left drawings of FIGS. 8A and 8B, the torque applied to the ankle portion 111 by the elastic member 131 is greater than the torque applied by the motor 151. Therefore, the sign of the power output by the motor 151 is opposite to that of the power output by the entire ankle portion 111.

The elastic force (for example, a spring constant) of the elastic member 131 is not limited to the elastic force exemplified above. The elastic force of the elastic member 131 can be properly selected so that the power necessary in the motor 151 is minimized in the range of the movement speed used in the movement support apparatus 1.

Here, in the movement support apparatus 1 according to the embodiment of the present disclosure, an elastic deformation amount of the elastic member 131 is changed by the rotation angle of the ankle portion 111 from the time point at which the ground contact plate 122 comes into contact with the ground surface and the ankle portion 111 and the transmission portion 126 engage with each other. On the other hand, when the movement speed is faster, the step length of a human being naturally increases. Therefore, the angle of the ankle joint at the time of the contact with the ground surface naturally increases, and thus the rotation angle of the ankle portion 111 also increases at the time of walking.

Accordingly, in the movement support apparatus 1 according to the embodiment of the present disclosure, as the movement speed becomes faster and the rotation angle of the ankle portion 111 increases, the elastic deformation amount of the elastic member 131 can be increased and the torque applied to the ankle portion 111 can be increased. As illustrated in FIGS. 8A to 8C, as the movement speed is faster, the power necessary in the ankle portion 111 increases. Therefore, in the movement support apparatus 1 according to the embodiment of the present disclosure, the torque applied from the elastic member 131 to the ankle portion 111 can be automatically increased according to the movement speed.

When a human being ascends or descends stairs, the feet of the human being come into contact with the stairs from the side of the tips of the toes in an operation of the lower limbs unlike the case described with reference to FIG. 2. In the movement support apparatus 1 according to the embodiment of the present disclosure, the ankle portion 111 and the transmission portion 126 come into contact with each other when the ground contact plate 122 on the side of the tip of the toe comes into contact with the ground surface. Therefore, even when the foot comes into contact with the ground surface from the tips of the toes, the force can be likewise transmitted to the ankle portion 111. Accordingly, the movement support apparatus 1 according to the embodiment of the present disclosure can be properly used even when a human being ascends or descends stairs.

<5. Conclusion>

As described above, in the movement support apparatus 1 according to the embodiment of the present disclosure, the elastic member 131 and the ankle portion 111 come into contact with each other and the force from the elastic member 131 is transmitted to the ankle portion 111 when the ground contact unit 121 comes into contact with the ground surface. Further, when the ground contact plate 122 is uncoupled from the ground surface, the movement support apparatus 1 releases the transmission of the force from the elastic member 131 to the ankle portion 111 by releasing the contact between the transmission portion 126 and the ankle portion 111. Accordingly, the movement support apparatus 1 according to the embodiment of the present disclosure can apply the force from the elastic member 131 to the ankle portion 111 when the power is most necessary in the ankle portion 111.

The movement support apparatus 1 according to the embodiment of the present disclosure applies the force from the elastic member 131 to the ankle portion 111 when the power is most necessary in the ankle portion 111, thereby reducing the maximum output of the motor 151. Accordingly, in the movement support apparatus 1 according to the embodiment of the present disclosure, it is possible to reduce the size and the weight of the motor 151. Further, it is possible to reduce the load on the user 3.

In the movement support apparatus 1 according to the embodiment of the present disclosure, the entire size of the movement support apparatus 1 can also be reduced by reducing the size of the motor 151. Accordingly, the movement support apparatus 1 according to the embodiment of the present disclosure can also be applied to the user 3 who has had a smaller part amputated.

The preferred embodiment of the present disclosure has been described in detail with reference to the appended drawings, but the technical scope of the present disclosure is not limited to the example. It should be understood by those skilled in the art that various modifications, combinations, sub-combinations and alterations may occur depending on design requirements and other factors insofar as they are within the scope of the appended claims or the equivalents thereof.

In the above-described embodiment, the movement support apparatus 1 has been described as an artificial leg, but embodiments of the present disclosure are not limited to the example. For example, the movement support apparatus 1 may be movement support equipment for a user whose walking ability is lowered due to aging, muscle weakness, or the like or may be a movement apparatus included in a lower limb of a robot or the like performing bipedal walking.

Additionally, the present technology may also be configured as below.

(1) A movement support apparatus including:
  a lower limb coupling portion configured to be coupled to a lower limb;
  an elastic member;
  a ground contact unit configured to include a ground contact plate coming into contact with a surface and a transmission portion transmitting force generated by the elastic member; and
  an ankle portion configured to be installed between the lower limb coupling portion and the ground contact unit,
  wherein the ground contact unit is installed to be displaceable between a position at which the transmission portion comes into contact with the ankle portion and a position at which the transmission portion is uncoupled from the ankle portion.
(2) The movement support apparatus according to (1),
  wherein the ground contact unit performs the displacement around a coupling point, and
  wherein the ground contact plate and the transmission portion are installed on a same side with respect to the coupling point.
(3) The movement support apparatus according to (1) or (2),
  wherein the ground contact plate is a toe tip ground contact plate coming into contact with the surface on a front side in a movement direction, and
  wherein the movement support apparatus further includes a heel-side ground contact plate configured to come into contact with the surface on a rear side in the movement direction.
(4) The movement support apparatus according to any one of (1) to (3), wherein the transmission portion includes a rack gear and the ankle portion includes a pinion gear engaging with the rack gear.
(5) The movement support apparatus according to any one of (1) to (4), wherein the transmission portion includes an ankle-side transmission portion located on a side of the ankle portion and an elastic-member-side transmission portion located on a side of the elastic member and configured to be separated from the ankle-side transmission portion.
(6) The movement support apparatus according to (5),
  wherein the ankle-side transmission portion and the elastic-member-side transmission portion are coupled through a coupling member with elasticity.
(7) The movement support apparatus according to any one of (1) to (6), further including:
  an actuator configured to apply force to the ankle portion.
(8) The movement support apparatus according to (7),
  wherein the actuator is a motor.
(9) The movement support apparatus according to (7), further including:
  a conversion portion configured to convert the force of the actuator to be applied to the ankle portion.
(10) The movement support apparatus according to (9),
  wherein the conversion portion is strain wave gearing.
(11) The movement support apparatus according to any one of (7) to (10), further including:
  at least one of an angle sensor configured to detect an angle of the ankle portion, a torque sensor configured to detect torque applied to the ankle portion, or a posture sensor configured to detect an inclination of the ankle portion,
  wherein the actuator controls an output of the actuator based on an output of the sensor.
(12) The movement support apparatus according to any one of (1) to (11), wherein the elastic member is one of a coil spring, a plate spring, a tension spring, or an air spring.

What is claimed is:

1. A movement support apparatus comprising:
  a lower limb coupling portion configured to be coupled to a lower limb;
  an elastic member;
  a ground contact unit including a ground contact plate coming into contact with a surface and a transmission portion coupled to the elastic member and movably attached to the ground contact plate; and
  an ankle portion installed between the lower limb coupling portion and the ground contact unit,
  wherein the ground contact unit is rotatably coupled to the ankle portion at a coupling point and is installed to be displaceable relative to the ankle portion between a first position at which the transmission portion comes into contact with the ankle portion and a second position at which the transmission portion is uncoupled from the ankle portion,
  wherein the ground contact unit and transmission portion are disposed on a same side with respect to the coupling point, and
  wherein the ground contact unit, the transmission portion, and the ankle portion are configured and arranged such that displacement of the ground contact unit relative to the ankle portion due to a reactive force received by the ground contact unit from a ground surface causes the transmission portion to contact the ankle portion and the absence of a reactive force received by the ground contact unit from the ground surface causes the transmission portion to be uncoupled from the ankle portion, and such that, when the transmission portion is in contact with the ankle portion, first movement of the ankle portion causes the transmission portion to move relative to the ground contact unit, which movement of the transmission portion causes the elastic member to store energy for transmission to the ankle portion during second movement of the ankle portion.

2. The movement support apparatus according to claim 1,
  wherein the ground contact plate is a toe tip ground contact plate coming into contact with the surface on a front side in a movement direction, and
  wherein the movement support apparatus further comprises a heel-side ground contact plate configured to come into contact with the surface on a rear side in the movement direction.

3. The movement support apparatus according to claim 1, wherein the transmission portion includes a rack gear and the ankle portion includes a pinion gear engaging with the rack gear when the transmission portion is in contact with the ankle portion.

4. The movement support apparatus according to claim 1, wherein the transmission portion includes an ankle-side transmission portion located on a side of the ankle portion and an elastic-member-side transmission portion located on a side of the elastic member and configured to be separated from the ankle-side transmission portion.

5. The movement support apparatus according to claim 4, wherein the ankle-side transmission portion and the elastic-member-side transmission portion are coupled through a coupling member with elasticity.

6. The movement support apparatus according to claim 1, further comprising:
   an actuator configured to apply force to the ankle portion.

7. The movement support apparatus according to claim 6, wherein the actuator is a motor.

8. The movement support apparatus according to claim 6, further comprising:
   a conversion portion configured to convert the force of the actuator to be applied to the ankle portion.

9. The movement support apparatus according to claim 8, wherein the conversion portion is strain wave gearing.

10. The movement support apparatus according to claim 6, further comprising:
    at least one of an angle sensor configured to detect an angle of the ankle portion, a torque sensor configured to detect torque applied to the ankle portion, or a posture sensor configured to detect an inclination of the ankle portion,
    wherein the actuator controls an output of the actuator based on an output of the sensor.

11. The movement support apparatus according to claim 1, wherein the elastic member is one of a coil spring, a plate spring, a tension spring, or an air spring.

* * * * *